US005695930A

United States Patent [19]
Weinstein et al.

[11] Patent Number: 5,695,930
[45] Date of Patent: Dec. 9, 1997

[54] HIV TEST KIT METHOD FOR DETECTING ANTI-HIV-I ANTIBODIES IN SALIVA

[76] Inventors: David E. Weinstein, 1622 Myrtle Ave., San Diego, Calif. 92103; Trevor J. Kilpatrick, 8750 Villa La Jolla Dr., Apt. 67, La Jolla, Calif. 92037

[21] Appl. No.: 692,445

[22] Filed: Aug. 5, 1996

Related U.S. Application Data

[63] Continuation of Ser. No. 337,670, Nov. 10, 1994, abandoned.

[51] Int. Cl.$^6$ ..................... C12Q 1/70
[52] U.S. Cl. ............... 435/5; 435/7.1; 435/7.72; 435/7.9; 435/7.92; 435/974; 436/518; 436/528; 436/531; 436/800; 436/810
[58] Field of Search .................. 435/5, 7.1, 7.6, 435/7.7, 7.72, 7.9, 7.92, 968, 974, 975; 436/518, 528, 531, 800, 810

[56] References Cited

U.S. PATENT DOCUMENTS

| | | | |
|---|---|---|---|
| 4,135,884 | 1/1979 | Shen | 422/59 |
| 4,299,916 | 11/1981 | Litman et al. | 435/6 |
| 4,305,924 | 12/1981 | Piasio | 424/1 |
| 4,444,880 | 4/1984 | Tom | 435/7 |
| 4,853,325 | 8/1989 | Voidan et al. | 435/5 |
| 4,923,798 | 5/1990 | LeMoine et al. | 435/5 |

FOREIGN PATENT DOCUMENTS

| | | | |
|---|---|---|---|
| 1298782 | 4/1992 | Canada | G01N 33/569 |
| 0289339 | 2/1988 | European Pat. Off. | G01N 33/569 |
| WO 88/10272 | 12/1988 | WIPO | C07K 17/02 |
| WO 93/03376 | 2/1993 | WIPO | G01N 33/569 |
| WO 93/11434 | 6/1993 | WIPO | G01N 33/543 |
| WO 93/22682 | 11/1993 | WIPO | G01N 33/569 |

OTHER PUBLICATIONS

Sangare et al. "Saliva Can Show Seroconversion", International Conference on AIDS, (7–12 Aug. 1994). vol. 10, No. 1, pp. 231 (Abstract No. PB0352).

Sangare et al. "Saliva Levels of HIV–1 Antibodies During Seroconversion", International Conference on AIDS, (7–12 Aug. 1994). vol. 10, No. 1, pp. 229 (Abstract No. PB0345).

Sun et a. "Secretory and Systemic Immunity in HIV–Infected Individuals", International Conference on AIDS, (1989). vol. 5, pp. 444 (Abstract No. Th.B.P.171).

Gosling. "A Decade of Development in Immunoassay Methodology", Clinical Chemistry, vol. 36, No. 8(Aug. 1990), pp. 1408–1427.

R.C. Gallo, "The Aids Virus,"*Scientific American*, 256:47 (1987).

S. Crowe and J. Mills, "Infections of the Immune System," Chapter 55, in: *Basic and Clinical Immunology*, 7th Ed. (D.P. Stites and A.I. Terr, Eds.), pp. 697–711 (1991).

L. Ratner et al., "Complete Nucleotide Sequence of the AIDS Virus, HTLV–III," *Nature* 313:277–284 (1985).

M. Popovic et al., "Detection, Isolation, and Continuous Production of Cytopathic Retroviruses (HTLV–III) from Patients with AIDS and Pre–AIDS," *Science*, 224:497–500 (1984).

F. Barin et al., "Virus Envelope Protein of HTLV–III Represents Major Target Antigen for Antibodies in AIDS Patients," *Science* 228:1094–96 (1985).

N.T. Constantine, et al., "Diagnostic usefulness of five screening assays for HIV in an East African city where the prevalence of infection is low,"*AIDS* 3:313–317 (1989).

M.A. Fischl et al., "Evaluation of heterosexual partners, children and household contacts of adults with AIDS," *JAMA* 257:640–644 (1987).

D.W. Archibald et al., "Antibodies to human T–lymphotropic virus type III (HTLV–III) in saliva of acquired immunodeficiency syndrome (AIDS) patients and in persons at risk for AIDS," *Blood* 67:831–834 (1986).

I.D. Mandel, "The diagnostic uses of saliva," *J. Oral Pathol. and Medicine* 19:119–125 (1990).

A.M. Johnson et al., "HIV surveillance by testing saliva," *AIDS* 2:369–371 (1988).

J.V. Parry, "Simple and reliable salivary tests for HIV and Hepatitis A and B virus diagnosis and surveillance," *Annals New York Acad. Sci.*, 694:216–233 (1993).

K. Stark et al., "Sensitivity of HIV antibody detection in saliva," *Med. Microbiol. Immunol.* 182:147–151 (1993).

J.A. Connell et al.,"Novel assay for the detection of immunoglobulin G antihuman immunodeficiency virus in untreated saliva and urine," *J. Med. Virol.*, 41:159–164 (1993).

S. Matsuda et al., "Characteristics of IgA antibodies against HIV–1 in sera and saliva from HIV–seropositive individuals in different clinical stages," *Scand. J. Immunol.* 38:428–434 (1993).

M. Urquia et al., "Detection of anti–HIV antibodies in saliva," *J. Oral. Pathol. Med.* 22:153–156 (1993).

J.V. Parry et al., "Sensitive assays for viral antibodies in saliva: An alternative to tests on serum," *Lancet* 2:72–75 (1987).

M.B. Vasudevachari et al., "Detection of antibodies to human immunodeficiency virus type I in whole blood and saliva by using a passive hemagglutination test," *J. Clin. Microbiol.* 27:2384–2385 (1989).

D.W. Archibald and C.A. Hebert, "Salivary detection of HIV–1 antibodies using recombinant HIV–1 peptides," *Virol. Immunol.* 4:17–22 (1991).

F.M. Behets et al., "Detection of Salivary HIV–1–Specific IgG Antibodies in High Risk Populations in Zaire," *J. Acq'd Immune Deficiency Syndromes* 4:183–187 (1991).

(List continued on next page.)

*Primary Examiner*—Donald E. Adams
*Assistant Examiner*—Jeffrey Stucker
*Attorney, Agent, or Firm*—Medlen & Carroll, LLP

[57] ABSTRACT

A rapid and accurate test kit is discussed for the detection of antibodies to HIV in saliva. The identification of antibodies to HIV in the saliva of seropositive individuals is shown using a test kit that requires no special machinery or skill and can be conducted by a single person in the privacy of their own home.

14 Claims, 2 Drawing Sheets

OTHER PUBLICATIONS

P. Holmstrom et al., "HIV Antibodies in Whole Saliva Detected by ELISA and Western Blot Assays," *J. Med. Virol.* 30:245–248 (1990).

M.B. Vasudevachari et al., "Envelope–Specific Antibodies in the Saliva of Individuals Vaccinated with Recombinant HIV–1 gp160," *J. Acq'd. Immune Defic. Syndr.* 5:817–821 (1992).

HIV TEST KIT METHOD FOR DETECTING ANTI-HIV-I ANTIBODIES IN SALIVA

This a continuation of application Ser. No. 08/337,670, now abandoned, filed on Nov. 10, 1994.

FIELD OF THE INVENTION

The present invention relates to the use of solid phase immunoassay for the detection of anti-HIV antibodies in saliva.

BACKGROUND OF THE INVENTION

Acquired immune deficiency syndrome (AIDS) has been described as the first great pandemic of the second half of the twentieth century. See R. C. Gallo, Scientific American, 256:39 (1987).

Human immunodeficiency virus (HIV) is the etiologic agent of AIDS. See S. Crowe and J. Mills in *Basic and Clinical Immunology*, 7th Ed. (D. P. Stites and A. I. Terr, Eds.), pp. 697–711 (1991). A complete sequencing of the HIV genome indicates that it comprises the same overall gag-pol-env organization as other retroviruses. See L. Ratner et al., Nature 313:277 (1985). The virus invades a host cell and uses the host cell's machinery to replicate itself.

The detection of HIV in human peripheral blood cells is now well-documented. The first assays involved isolation and culture of the virus. See M. Popovic et al., Science 224:497 (1984). However, the process takes 3–4 weeks and has low sensitivity. Subsequent assays measured anti-viral antibody produced by human immune cells that contacted the virus. See F. Barin et al., Science 228:1094 (1985).

At the present time, the most widely used methods to detect the presence of anti-HIV antibodies involve the detection of these antibodies in blood. However, the use of blood samples to detect anti-HIV antibodies involves significant health risks to both health care workers and blood donors, significant economic costs in sample obtainment, transportation and handling, and frequently leads to problems in obtaining voluntary samples from donors. See N. T. Constantine, et al., "Diagnostic usefulness of five screening assays for HIV in an East African city where the prevalence of infection is low," AIDS 3:313–317 (1989).

Epidemiological evidence and laboratory studies have shown that HIV is not transmittable in saliva. See M. A. Fischl et al., "Evaluation of heterosexual partners, children and household contacts of adults with AIDS," JAMA 257:640–644 (1987).

However, while HIV is not transmitted in saliva, it has been well documented that antibodies to HIV are present in saliva. See D. W. Archibald et al., "Antibodies to human T-lymphotropic virus type III (HTLV-III) in saliva of acquired immunodeficiency syndrome (AIDS) patients and in persons at risk for AIDS," Blood 67:831–834 (1986). Because saliva represents an anti-HIV antibody-containing bodily fluid that is both non-infectious and easily obtainable, it has been suggested that saliva be used as a source for screening for anti-HIV antibodies. See I. D. Mandel, "The diagnostic uses of saliva," J. Oral Pathol. and Medicine 19:119–125 (1990).

However, attempts to modify commercially available HIV antibody assays in order to detect anti-HIV antibodies in saliva, as opposed to blood, have met with limited success with regard to the sensitivity of the assay. For example, Johnson et al. assayed the Wellcozyme HIV monoclonal ELISA, the Abbott recombinant DNA ELISA, and the Fujirebo particle agglutination test using whole saliva. A.M. Johnson et al., "HIV surveillance by testing saliva," AIDS 2:369–371 (1989). Johnson et al. reported that while the ELISA assays were highly specific (greater than 99%), they were only moderately sensitive (90.9% and 82.0%, respectively), even when the cutoff allowance of the assay was lowered 20% for saliva samples. Further, Johnson et al. reported that the specificity of the particle agglutination assay was only 84%.

More recently, ELISA methods have been developed wherein the sensitivity of the detection of anti-HIV antibodies in saliva has been improved using modifications of kits developed for the detection of anti-HIV antibodies in blood. Reviewed in: J. V. Parry, "Simple and reliable salivary tests for HIV and Hepatitis A and B virus diagnosis and surveillance," Annals New York Acad. Sci., 694:216–233 (1993); see also: K. Stark et al., "Sensitivity of HIV antibody detection in saliva," Med. Microbiol. Immunol. 182:147–151 (1993); J. A. Connell et al.,"Novel assay for the detection of immunoglobulin G antihuman immunodeficiency virus in untreated saliva and urine," J. Med. Virol., 41:159–164 (1993); S. Matsuda et al., "Characteristics of IgA antibodies against HIV-1 in sera and saliva from HIV-seropositive individuals in different clinical stages," Scans. J. Immunol. 38:428–434 (1993); and M. Urquia et al., "Detection of anti-HIV antibodies in saliva," J. Oral. Pathol. Med. 22:153–156 (1993). In addition, a commercial anti-HIV assay kit has been developed for the purpose of detecting anti-HIV antibodies in saliva (Wellcozyme HIV 1+2 GACELISA, Murex Diagnostics, Darthord, United Kingdom).

Antibodies to HIV in saliva have also been detected using other immunoassays, including radioimmunoprecipitation (D. W. Archibald et al. (1986), supra), IgG antibody capture radioimmunoassay (J. V. Parry et al., "Sensitive assays for viral antibodies in saliva: An alternative to tests on serum," Lancet 2:72–75 (1987)), passive hemagglutination (M. B. Vasudevachari et al., "Detection of antibodies to human immunodeficiency virus type I in whole blood and saliva by using a passive hemagglutination test," J. Clin. Microbiol. 27:23–84–2385 (1989), latex agglutination (C. H. Riggin, European Patent Appl'n. Pub. No. 0,289,339 (Feb. 11, 1988)), and ELISA using recombinant HIV peptides (D. W. Archibald and C. A. Hebert, "Salivary detection of HIV-1 antibodies using recombinant HIV-1 peptides," Virol. Immunol. 4:17–22 (1991)).

Importantly, all of the HIV detection methods discussed above involve the use of at least one immunoassay that requires the use of sophisticated and expensive scientific equipment (such as an automated ELISA system) that must be operated by highly trained personnel in a laboratory setting. Because of this limitation, existing assays for salivary anti-HIV antibodies are limited by the high cost of machinery, laboratory space and personnel.

Further, because the assays must be performed in a laboratory that is often located at a different location from the sample collection site, existing assays for the detection of salivary anti-HIV antibodies are hampered by the cost of sample transportation, the risk of sample loss or degradation during transportation, and the risk of reporting error due to the possibility of mixing up samples during transportation.

The need to transport samples to a remote location where the HIV assay will be conducted also necessarily evokes both questions and concerns regarding the confidentiality and accuracy of reporting on a patient's AIDS status. Indeed, fear regarding the confidentiality and accuracy of the reporting of AIDS test results is widely believed to be a major reason why people refuse to be tested for anti-AIDS virus antibodies.

The benefits of AIDS testing are myriad and include, inter alia, i) protecting the health of the infected, yet asymptomatic patient, ii) enhancing the mental health and security of both infected and asymptomatic patients, as well as non-infected, at risk individuals, and iii) preventing both horizontal and vertical transmission of the AIDS virus through the identification and education of infected individuals.

Detecting anti-HIV antibodies in saliva offers the distinct advantage that HIV is not transmitted in saliva, as opposed to blood. However, existing methods of detecting anti-HIV antibodies in saliva are significantly limited in that the assays require that the saliva samples, after collection, be transported to a laboratory facility where they are subjected to expensive and elaborate immunoassays. This requisite step of laboratory analysis adds additional cost to the method of testing and raises significant concerns regarding both the confidentiality and the accuracy of reporting a patient's HIV status.

What is needed is an inexpensive assay for anti-HIV antibodies in saliva that allows for the detection of anti-HIV antibodies without the need for a laboratory immunoassay. Ideally, what is needed is an HIV assay that can be personally performed by the saliva donor, in the privacy of the donor's own home, without the need to involve any other person in the testing process; thus assuring an inexpensive HIV assay that is both accurate and highly confidential.

SUMMARY OF THE INVENTION

The present invention relates to the use of solid phase immunoassay for the detection of anti-viral antibodies in saliva. A viral disease contemplated is the human immunodeficiency virus (HIV). Several cell lines which produce the virus are available, such as, for example, CR10/N1T (Catalog No. 392, NIH AIDS Research and Reference Reagent Program).

The present invention contemplates a method for detecting exposure to human immunodeficiency virus in a mammal comprising contacting a mammalian mucous secretion with human immunodeficiency virus antigen bound to a nitrocellulose-containing solid support for a time and under conditions sufficient for an antibody in the mucous secretion specific to human immunodeficiency virus antigen to form a complex therewith and then subjecting the complex to detecting means in order to detect the complex. Typically, the contacting time will be in the range of 20 to 45 minutes at room temperature and preferably, about thirty minutes. Preferably, the mammal is a human. The human immunodeficiency virus antigen is selected from the group consisting of human immunodeficiency virus type I, human immunodeficiency virus type II or human immunodeficiency virus type III. In a preferred embodiment, the human immunodeficiency virus antigen is the p17 protein (SEQ ID NO:2) of human immunodeficiency virus type I. Also in a preferred embodiment, the mucous secretion is saliva.

In one embodiment of the method, the detecting means is a second antibody conjugated to a reporter molecule. As used herein, a reporter molecule is a compound that either can itself be detected or that promotes a reaction with another compound that can be detected. For example, one type of reporter molecule is an enzyme that promotes a reaction which can be detected by a change in color of the reactants. Preferably, the reporter molecule is an enzyme and, more preferably, the enzyme is alkaline phosphatase. In an alternative embodiment, the reporter molecule is a fluorophore (e.g., fluoroscein).

Also contemplated is a method for detecting exposure to human immunodeficiency virus in a fasting human comprising: a) providing saliva from a fasting human, wherein the saliva is suspected to contain an antibody for a human immunodeficiency virus antigen; b) contacting the saliva with a human immunodeficiency virus antigen immobilized on a solid support for a time and under conditions sufficient for the antibody to form a complex with the immobilized human immunodeficiency virus antigen; c) contacting the complex with an effective amount of a second antibody conjugated to a reporter molecule; and d) detecting binding of the second antibody to the complex. It is also contemplated that the fasting is for at least about one hour but longer times are also appropriate. In a preferred embodiment, the solid support contains nitrocellulose. In one embodiment, the reporter molecule is a fluorophore and the detecting comprises measuring fluorescence of the fluorophore. Preferably, the reporter molecule is an enzyme and the detecting comprises measuring the result of an enzymatic reaction.

The present invention also contemplates a test kit for detecting the presence, in a mammalian mucous secretion, of an antibody to a human immunodeficiency virus antigen, wherein the test kit comprises: a) a solid support having an antigen from a human immunodeficiency virus immobilized thereupon; and b) means for detecting whether the antibody in the mammalian mucous secretion is bound to the immobilized human immunodeficiency virus antigen. The human immunodeficiency virus antigen is selected from the group consisting of human immunodeficiency virus type I, human immunodeficiency virus type II or human immunodeficiency virus type III. In a preferred embodiment, the human immunodeficiency virus antigen is p17 protein (SEQ ID NO:2) of human immunodeficiency virus type I. Preferably, the mucous secretion is saliva. In one embodiment, the detecting means is a second antibody conjugated to a reporter molecule. Preferably, the reporter molecule is an enzyme and, more preferably, the reporter molecule is alkaline phosphatase. In an alternative embodiment, the reporter molecule is a fluorophore.

The present invention also contemplates a test kit for detecting the presence, in a mammalian mucous secretion, of an antibody to a human immunodeficiency virus antigen, wherein the test kit comprises: a) a first compartment adapted to contain a solid nitrocellulose-containing support having human immunodeficiency virus antigens immobilized thereupon; b) a second compartment containing a conjugate comprising a secondary antibody specific for mammalian salivary antibodies conjugated to a reporter molecule; and c) a third compartment containing all standard reagents necessary for the reporter molecule to produce a signal. The human immunodeficiency virus antigen is selected from the group consisting of human immunodeficiency virus type I, human immunodeficiency virus type II or human immunodeficiency virus type III. Preferably, the human immunodeficiency virus antigen is p17 protein (SEQ ID NO:2) of human immunodeficiency virus type I. In one embodiment, the reporter molecule is an enzyme and preferably the reporter molecule is alkaline phosphatase. In an alternative embodiment, the reporter molecule is a fluorophore.

The present invention contemplates, in a preferred embodiment, detecting, in saliva, antibodies specific for HIV. In a preferred embodiment, HIV antigens are bound to a nitrocellulose-containing solid support. The antigen-bound solid support is then exposed to a source of saliva suspected of containing antibodies specific to HIV antigens. Following exposure to the saliva for a time sufficient for anti-HIV antibodies to bind to HIV antigens upon the support and create an antibody-antigen complex, the solid support is then rinsed free of unbound antibodies (e.g., non-specifically bound antibodies). Next, in a preferred embodiment, a second antibody labeled with a reporter molecule is exposed to the antigen-antibody complex. In a preferred embodiment, the second antibody is specific for human antibodies, assayed from saliva. Finally, the strip is again rinsed to remove unbound (e.g., excess) second antibody. The strip is then exposed to a means for detecting the presence of bound second antibody. In a preferred embodiment an enzymatic or fluorogenic assay would be employed as the means for detecting bound second antibody.

Binding of the second antibody would be indicative of the presence of salivary antibodies specific for HIV, since the second antibody would not bind to the strip absent the initial binding of anti-HIV salivary antibodies to the HIV antigens bound on the solid support. The presence of salivary antibodies specific for HIV would be indicative that the saliva donor had been exposed to HIV.

Also in a preferred embodiment, it is contemplated that both positive and negative controls be employed in the same assay. In a preferred embodiment, the positive control would be goat anti-human antibody bound to a specific region of the nitrocellulose-containing solid support. Alternatively, human IgG, IgM and IgA may be used as positive controls. In a preferred embodiment, the negative control would be the absence of bound HIV antigen at a specific region of the nitrocellulose-containing solid support.

Significantly, the assay for the detection of binding of the second antibody is contemplated to be such that it can be carried out without the use of laboratory equipment or trained personnel. In a preferred embodiment, the human saliva donors can perform the assay and observe the results themselves, in the privacy of their own homes, without need of involving another party. In a preferred embodiment, the assay indicator is colorogenic, such that a positive result can be readily determined by visual inspection of the solid support.

DESCRIPTION OF THE INVENTION

The present invention relates to the use of solid phase immunoassay for the detection of anti-HIV antibodies in saliva. As discussed above, HIV is not transmitted through saliva, however, the saliva of individuals exposed to HIV contains anti-HIV antibodies. Thus, saliva is a safe and easily obtainable source of anti-HIV antibodies.

However, as also discussed above, current methods to assay saliva for the presence of anti-HIV antibodies require an assay step that requires the operation of expensive machinery by highly trained personnel in a laboratory facility. Not only does this requirement drive up the cost of AIDS screening, but, in addition, it raises serious concerns regarding the confidentiality and accuracy of reporting AIDS testing results.

The present invention takes advantage of the safety and ease of using saliva as a source of bodily fluid suspected of containing anti-HIV antibodies, in an assay that can easily and accurately be conducted by the saliva donor personally, in the donor's own home, without the need for an expensive assay at a remote laboratory.

This invention eclipses the prior art by replacing complicated assays such as ELISA plate technology, radioimmunoassays and agglutination assays for the detection of salivary anti-HIV antibodies with the novel use of a nitrocellulose-containing solid support to bind HIV antigens. The use of this novel nitrocellulose-containing support (See FIG. 1) allows an immunoassay for the presence of anti-HIV antibodies in saliva to be conducted easily and accurately by the saliva donor personally, without the need for an expensive assay at a remote laboratory.

Because the HIV antigen is fixed upon a nitrocellulose-containing solid support (100), the support can be directly applied to a saliva sample in, for example, a collection tube (200), or, for example, directly in the mouth. This eliminates the need to transfer the saliva sample (250) to a separate assay chamber, such as the well of an ELISA plate.

Figure 1:
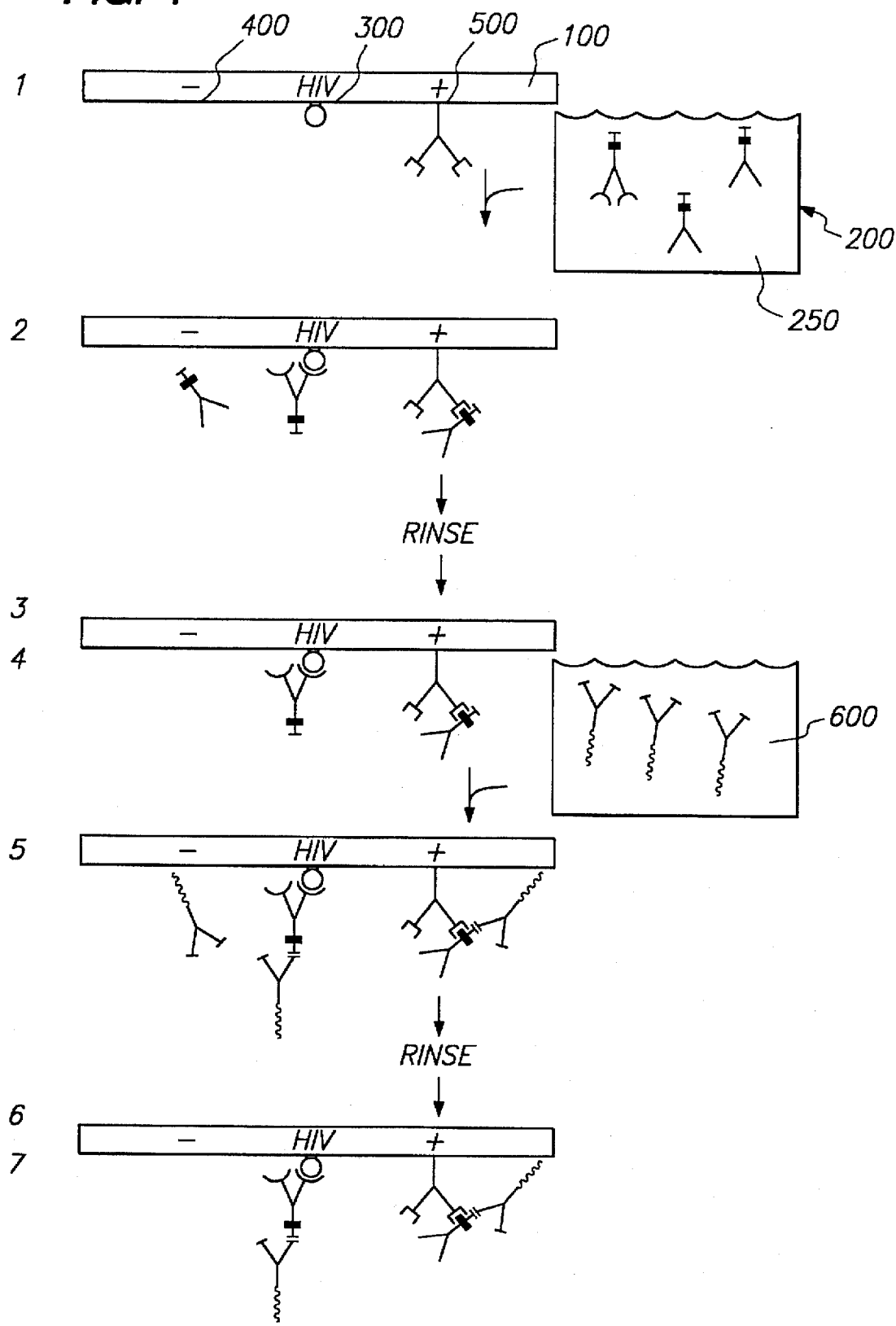
FIG. 1 is a schematic of the sandwich immunoassay of the preferred embodiment.

Further, because the antigen-antibody binding is conducted directly upon a solid support (100), sequential sandwich immunoassay steps including rinsing between steps and the binding of the second antibody and development of the indicator reaction can be easily performed without the need for expensive automation and skill (See FIG. 1). At step 1, the sample of saliva (250) containing antibody is applied to (i.e. placed in contact with) the solid support. Saliva may contain anti-HIV antibody [ ⱴ ] or other human antibodies [ Y ]. A solution (600) containing the second antibody [ Y ] is placed in contact (See Step 4) with the test (300) and control (400, 500) surfaces of the solid support after rinsing off (See Step 3) excess saliva and unbound antibody from the previous step but leaving bound anti-HIV antibody. In a preferred embodiment, the second antibody is goat anti-human IgG, IgA and IgM, conjugated to alkaline phosphatase. Unbound second antibody is rinsed off (See Step 6) and a substrate for alkaline phosphatase is added in solution (Not shown). As used herein, substrate refers to a substance that is hydrolyzed in the presence of the enzyme. The substrate can be a NBT/X phos substrate (commercially available from Boehringer Mannheim) in solution, which turns blue after hydrolysis. Other substrates of alkaline phosphatase are also appropriate (e.g., p-nitrophenyl phosphate). These steps are represented schematically in FIG. 1, wherein anti-HIV antibodies in saliva bind to HIV antigen on the solid support (100), then secondary antibodies directed against human immunoglobulins bind to both the anti-HIV antibodies and to the positive control region (500) which contains goat anti-human antibody [ ⱴ ] attached indirectly to the solid support.

The present invention demonstrates high sensitivity in detecting anti-HIV antibodies. It is believed that an important factor in achieving this level of sensitivity is fasting by the subject prior to performing the assay. Indeed, the lack of sensitivity in previous saliva antibody assays is probably due to a lack of appreciation of the fasting factor.

Figure 3:
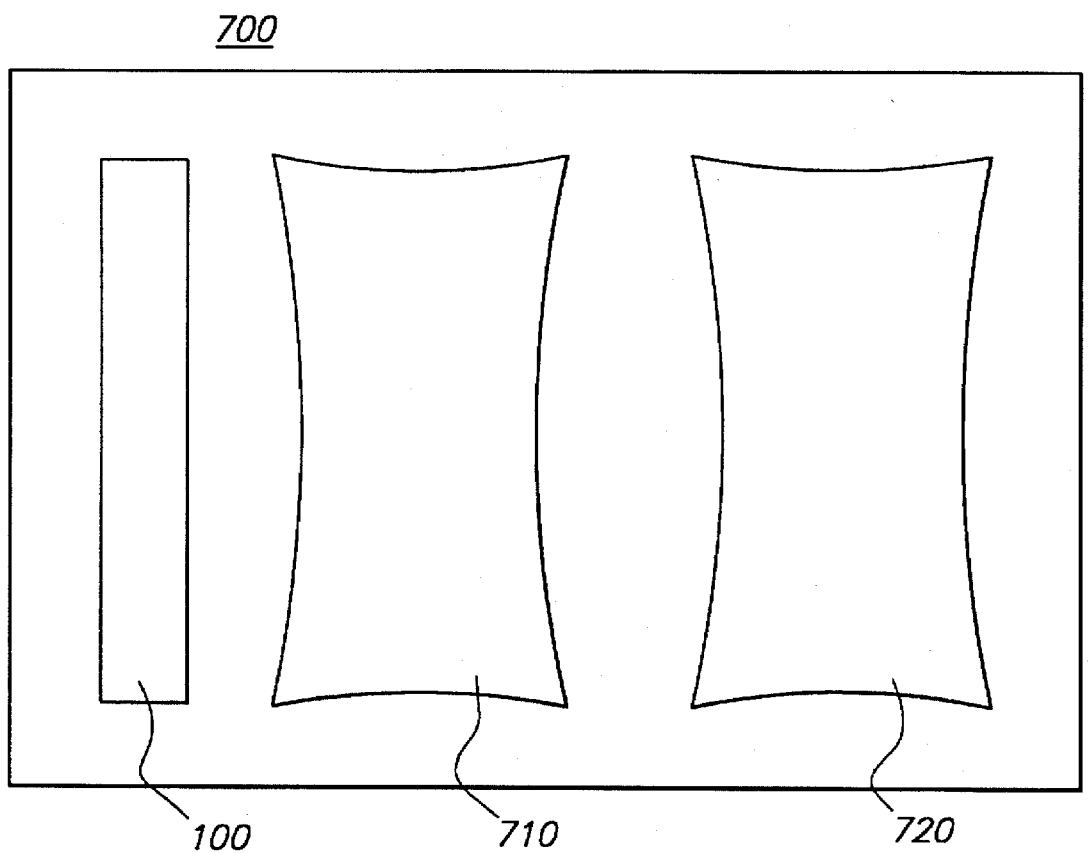
FIG. 3 represents one embodiment of a test kit.

It is further contemplated that the instant nitrocellulose-containing solid support will be packaged in a kit which will contain all reagents necessary to allow one to perform the complete immunoassay at home, at room temperature and with only the need to provide a source of tap water. (See FIG. 3) Such a kit (700) is envisioned to contain i) a nitrocellulose-coated surface (100) on which HIV antigens are bound, ii) a first pouch (710) containing a second antibody conjugated to a reporter molecule in an appropriate solution for use in the assay, and iii) a second pouch (720) containing all reagents necessary to generate a signal from the second antibody when this antibody is bound to salivary antibodies that are bound to HIV antigens that are bound to the solid support.

Figure 2:
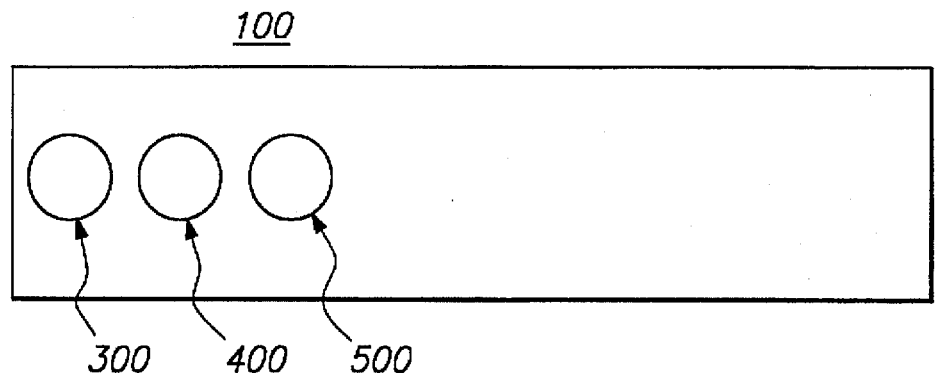
FIG. 2 is a drawing of one embodiment of the solid support.

It is further envisioned that the nitrocellulose-coated solid support will have three distinct regions, a first region (300) having bound HIV antigen as the test surface, a second region (500) having a bound positive control as a comparison surface and a third region (400) having no bound HIV antigen, serving as a negative control (See FIG. 2 for one example of a solid support having these three regions). A number of positive control proteins can be used. The preferred positive control protein is unconjugated antibody to human immunoglobulin. Other controls are possible. For example, when alkaline phosphatase serves as a reporter molecule, the positive control protein may be alkaline phosphatase bound to the nitrocellulose or alkaline phosphatase bound to a protein (e.g., bovine serum albumin or immunoglobulin) which is bound to the nitrocellulose. In this manner, the positive control protein will serve to confirm that substrate for alkaline phosphatase has been added appropriately. It is still further envisioned that in a preferred embodiment, each of the pouches that contain reagents would be separately labeled and sealed with a readily puncturable seal such that the kit could be operated in the following sequence: i) apply saliva to the solid support and incubate at room temperature, ii) rinse the solid support under cool tap water to remove salivary antibodies not bound to HIV antigens on the solid support, iii) puncture the second pouch containing second antibody, allow the contents to thoroughly wet the solid support, and incubate at room temperature, iv) rinse with cool tap water to remove the second antibody not bound to salivary antibody, v) puncture the pouch containing reagents necessary to generate a signal from the bound second antibody, allow the reagents to thoroughly wet the solid support surface, and incubate at room temperature to observe the results. The use of "dip sticks" and other solid supports has been described in the context of an immunoassay for a limited number of antigens; notably not including either HIV antigens or anti-HIV antibodies. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. Notably however, these patents do not address the specific detection of antibodies to HIV in saliva.

Litman et al. (U.S. Pat. No. 4,299,916), broadly describes an assay method wherein the presence of a labeled immunological pair (consisting of a ligand and a receptor) on a solid support is distinguished from soluble labeled reagents. Significantly, this patent does not address the specific detection of antibodies to HIV in saliva.

Patent Cooperation Treaty (PCT) Application No. WO 93/11434 (issued to J. S. Sangha and R. S. Shea) describes an apparatus and method for determining, during collection of a saliva sample, whether a selected amount of saliva is deposited upon a solid support. While the application suggests that the collection device could be used in the context of collecting saliva samples suspected of containing anti-HIV antibodies, unlike the instant invention, the PCT application suggests that once the saliva is collected, it can be eluted from the collection surface for analysis in traditional immunoassays such as ELISA.

PCT Application No. WO 88/10272 (issued to G. A. Nicholson) describes a method of transporting samples of bodily fluids suspected of containing HIV and anti-HIV antibodies, wherein the samples are dried upon an absorbent surface prior to transport to a central laboratory. While the application does mention that the absorbent surface could include nitrocellulose, the application only addresses the use of the absorbent surface for transporting the samples. Once at a central laboratory, the patent describes the elution of the sample from the surface to be analyzed by traditional assays for HIV infection such as the ELISA-type Abbott Laboratories blood assay (ABBOTT HTLV-III EIA No. 1037).

PCT Application No. WO 93/22682 (issued to A. G. Sheard) describes the use of a nitrocellulose-containing solid support in the context of an immunoassay designed to detect the presence of antibodies to *Helicobacter pylori* in saliva. The patent discloses that a preparation of *H. pylori* antigens may be immobilized on a solid support such as a nitrocellulose strip, in the context of an immunoassay for the presence of anti-*H. pylori* antibodies. Significantly, the patent does not address the detection of anything other than anti-*H. pylori* antibodies in saliva.

Finally, U.S. Pat. No. 4,923,798 (issued to E. D. LeMoine, E. S. Bean and M. A. Vodian), U.S. Pat. No. 4,853,325 (Issued to M. A. Vodian, E. S. Bean and E. D. LeMoine) and Canadian Patent No. 1,298,782 (issued to M. A. Vodian, E. S. Bean and E. D. LeMoine) describe a test for the presence of feline leukemia virus (FeLV) and FeLV antigens in cat saliva. These patents describe a "probe" which contains a bibulous support. The "probe" is first placed into a cat's mouth where it absorbs a saliva sample. Then, a sandwich immunoassay to detect the presence of FeLV or FeLV antigens in the saliva is performed within the "probe." Significantly, these patents do not discuss the use of nitrocellulose as the solid support for the immunoassay (plastic is used), the technique is directed toward detecting viral particles and viral antigens in saliva, as opposed to anti-viral antibodies. Further, the patents do not discuss human viruses such as HIV.

The present invention provides a method and apparatus for the detection of antibodies to HIV in saliva that is rapid, accurate and can be performed by the saliva donor alone, in the privacy of the home. Moreover, none of the prior art appreciated the importance of fasting before saliva is tested.

The preferred solid matrix contains a thin layer of nitrocellulose upon either polystyrene or polyvinyl chloride, where the thin nitrocellulose layer is prepared by applying a 2.5% (w/v) solution of nitrocellulose in absolute methanol to a sheet of plastic.

The preferred HIV antigen to be fixed upon the nitrocellulose-containing solid support is the p17 matrix protein (SEQ ID NO:2) of HIV-1. The p17 protein, in a modified form, is commercially available (SEQ ID NO:1) (Intracel Corp., Cambridge, Mass.; Cat. No. 048001). The present invention also contemplates the ability to assay saliva for the presence of other antibodies to other human immunodeficiency viruses, as well as to antibodies to other types of viruses and other types of microorganisms.

The preferred second antibody is goat anti-human IgG, IgA and IgM, conjugated to alkaline phosphatase. In the preferred embodiment, the second antibody is conjugated to alkaline phosphatase as a labeling agent. However, it is not intended that the present invention be limited by the nature of the label used. The present invention contemplates the use of other reporters such as fluorophores.

EXPERIMENTAL

The following examples serve to illustrate certain preferred embodiments and aspects of the present invention and are not to be construed as limiting the scope thereof.

In the experimental disclosure which follows, the following abbreviations apply: mM (millimolar); μg (micrograms); ml (milliliters); μl (microliters); mm (millimeters); μm (micrometers); ° C. (degrees Centigrade); s (seconds); Tris (tris(hydroxymethyl)aminomethane); NaCl (sodium chloride); KCl (potassium chloride); MgCl$_2$ (magnesium chloride); w/v (weight to volume); Intracel (Intracel Corporation, Cambridge, Mass.).

The following examples are provided in order to demonstrate and further illuminate certain aspects of the practice of the invention.

EXAMPLE 1

Preparation Of Nitrocellulose-Containing Solid Support Test Strip

A nitrocellulose membrane, 0.2 μm or 0.45 μm pore size(Schleicher and Schuell, Keene, N.H.) was dissolved in absolute methanol (Fisher, Fairlawn, N.J.) to a final concentration of 2.5% (w/v).

Three 10 μl aliquots of the nitrocellulose solution were spotted onto a 0.015 inch thick strip of 6 mm ×65 mm high impact polystyrene (Ridout Plastics, San Diego, Calif.), or onto a 0.015 inch thick strip of 6 mm ×65 mm polyvinyl chloride (Ridout Plastics, San Diego, Calif.), and allowed to dry thoroughly. This procedure produced three small spots each consisting of a thin film of nitrocellulose bound to the solid support.

One spot, the positive control spot, was thoroughly wetted with about 1 μl of a 1:1000 dilution of goat anti-human IgG, IgA and IgM (Southern Biotechnology Associates, Birmingham, Ala.). A second spot, the negative control, was thoroughly wetted with about 1 μl of a 5% solution of bovine serum albumin (Sigma Chemical Co., St. Louis, Mo.). A third spot, the test spot, was thoroughly wetted with about 1 μl of a 0.75 μg/μl solution of the purified HIV matrix protein p17 (SEQ ID NO:2). Following the spotting, the proteins were allowed to adhere to the nitrocellulose in a humidified chamber, at room temperature, for 30 minutes.

Following the 30 minute incubation, the strip was then transferred to a blocking solution consisting of 5% non-fat milk (Carnation Corp., Los Angeles, Calif.), 5% normal goat serum (GibcoBrl, Gaithersburg, Md.), 0.1% Triton X-100 (Sigma Chemical Co., St. Louis, Mo.), all in phosphate buffered saline without calcium and magnesium (2.7 mM KCl, 1.2 mM KH$_2$PO$_4$, 138 mM NaCl, 8.1 mM Na$_2$HPO$_4$-7H$_2$O), and incubated at room temperature for 1 hour.

The test strips were then either used immediately, or could be stored at 4° C. for future use.

EXAMPLE 2

Detection Of Anti-HIV Antibodies In The Saliva Of HIV Seropositive Individuals

Eight HIV-1 seropositive individuals, known to be seropositive by previous Western blot analysis (Table 1), and five HIV-1 seronegative persons (Table 2) were chosen for this test. Both fasting and mid-meal samples were taken from each patient, as well as fresh samples, stored on ice prior to the test, and frozen samples, stored at -70° C. for up to two weeks prior to testing.

Each patient was asked to expectorate approximately 5 ml of saliva into a sterile 50 ml conical tube. For fasting samples, patients had fasted for at least 1 hour before providing saliva samples. For mid-meal samples, patients were provided with a meal consisting of a bagel and cream cheese. At the mid-point of the meal, when approximately one half of the sandwich was consumed, the subjects rinsed their mouths with water, swallowed the rinse, then waited 60 seconds before providing saliva samples.

The test strips were immersed in the saliva samples such that the entire surface, with the nitrocellulose-bound proteins, was in direct contact with the saliva. In order to reduce the volume of saliva required to fully wet the test strip surface, the tubes were laid at approximately a 70° angle. The test strips were incubated with the saliva samples for about 30 minutes at room temperature.

TABLE 1

SERO-POSITIVE SUBJECTS

| Subject | Age | Gender | Years Since Sero-Conversion | Health Re AIDS |
| --- | --- | --- | --- | --- |
| 1. MV | 40 | male | 4 | well |
| 2. SS | 29 | male | 2 | well |
| 3. RP | 34 | male | 3 | well |
| 4. JS | 32 | male | 3 | well |
| 5. VR | 39 | male | 5 | well |
| 6. ST | 27 | male | 3 | ARC |
| 7. RK | 35 | male | 4 | well |
| 8. RP | 34 | male | 3 | ARC |

TABLE 2

CONTROL SUBJECTS

| Subject | Age | Gender | Overall Health |
| --- | --- | --- | --- |
| 1. MW | 43 | female | well |
| 2. TK | 35 | male | well |
| 3. TP | 34 | male | well |
| 4. DW | 36 | male | liver transplant |
| 5. GH | 74 | male | well |

The test strips were then washed under cool gently running tap water for 1 minute, to remove unbound antibodies. The test strips were then incubated for 20 minutes at room temperature with goat anti-human IgG, IgA and IgM, conjugated to alkaline phosphatase (Southern Biotechnology Associates, Birmingham, Ala.), diluted 1:1000 in a blocking solution consisting of 5% non-fat milk (Carnation Corp., Los Angeles, Calif.), 5% normal goat serum (GibcoBrl, Gaithersburg, Md.), 0.1% Triton X-100 (Sigma Chemical Co., St. Louis, Mo.), all in phosphate buffered saline without calcium and magnesium (2.7 mM KCl, 1.2 mM KH$_2$PO$_4$, 138 mM NaCl, 8.1 mM Na$_2$HPO$_4$-7H$_2$O).

The test strips were again washed under cool gently running tap water for 1 minute, to remove unbound antibodies. The test strips were then incubated for 10 minutes in a NBT/X phos substrate (Boehringer Mannheim), diluted in 100 mM NaCl, 100 mM Tris-HCl, 20 mM MgCl$_2$ (all from Sigma Chemical Co., St. Louis, Mo.) pH 9.5. A blue spot similar in intensity to the positive control indicated a positive test for anti-HIV antibodies in the saliva, while a white spot, similar to the negative control, indicated a negative test.

The test results from fasting samples (Table 3) were in 100% correlation with the HIV serology of the sample donors. Eight of eight seropositive saliva donors tested positive for salivary anti-HIV antibodies in the test, while five of five seronegative saliva donors tested negative for anti-HIV antibodies in the test.

The mid-meal saliva samples (Table 3), however, were less effective in detecting anti-HIV antibodies in the saliva of seropositive donors; the test failed to detect anti-HIV antibodies in the saliva of two of eight seropositive individuals. Importantly, however, the test detected no false positives, with five of five seronegative donors producing a negative result in the test. There were no differences in the results of the tests between fresh samples and samples that had been frozen before being tested (Table 3).

From the above, it should be clear that the present invention provides a solid phase immunoassay for the detection of anti-HIV antibodies in saliva. The present invention demonstrates high sensitivity in detecting anti-HIV antibodies. It is believed that an important factor in achieving this level of sensitivity is fasting by the subject prior to performing the assay. Indeed, the lack of sensitivity in previous saliva antibody assays is probably due to a lack of appreciation of the fasting factor.

TABLE 3

| Sample | Positive Test for Anti-HIV Antibody | Negative Test for Anti-HIV Antibody |
| --- | --- | --- |
| Fresh Fasting Seropositive | 8/8 | 0/8 |
| Fresh Fasting Seronegative | 0/5 | 5/5 |
| Fresh Mid-Meal Seropositive | 6/8 | 2/8 |
| Fresh Mid-Meal Seronegative | 0/5 | 5/5 |
| Frozen Fasting Seropositive | 8/8 | 0/8 |
| Frozen Fasting Seronegative | 0/5 | 5/5 |
| Frozen Mid-Meal Seropositive | 6/8 | 2/8 |
| Frozen Mid-Meal Seronegative | 0/5 | 5/5 |

We claim:

1. A method for detecting antibodies to human immunodeficiency virus type I comprising contacting saliva from a fasting human with antigen consisting of p17 protein from human immunodeficiency virus type I bound to a nitrocellulose-containing solid support for a time and under conditions sufficient for an antibody in the saliva to said antigen to form a complex therewith and then subjecting the complex to detecting means in order to detect the complex.

2. The method of claim 1, wherein the mucous secretion is saliva.

3. The method of claim 1, wherein the detecting means is a second antibody, conjugated to a reporter molecule.

4. The method of claim 3, wherein the reporter molecule is an enzyme.

5. The method of claim 4, wherein the reporter molecule is alkaline phosphatase.

6. The method of claim 3, wherein the reporter molecule is a fluorophore.

7. The method of claim 1, wherein the mammal is a human.

8. A method for detecting exposure to human immunodeficiency virus type I in a fasting human comprising:

a) providing saliva from a fasting human, wherein said saliva is suspected to contain an antibody for a human immunodeficiency virus type I antigen;

b) contacting said saliva with a human immunodeficiency virus type I antigen immobilized on a solid support for a time and under conditions sufficient for said antibody to form a complex with said immobilized human immunodeficiency virus antigen;

c) contacting said complex with an effective amount of a second antibody conjugated to a reporter molecule; and d) detecting binding of said second antibody to said complex.

9. The method of claim 8 wherein said fasting is for at least about one hour.

10. The method of claim 8 wherein said solid support contains nitrocellulose.

11. The method of claim 8 wherein said reporter molecule is a fluorophore and said detecting comprises measuring fluorescence of said fluorophore.

12. The method of claim 8 wherein said reporter molecule is an enzyme and said detecting comprises measuring the result of an enzymatic reaction.

13. A method for detecting antibodies to human immunodeficiency virus type I in a fasting human comprising:

a) providing saliva from a fasting human, wherein said saliva is suspected to contain an antibody reactive with human immunodeficiency virus type I antigen;

b) contacting said saliva with antigen consisting of p17 protein of human immunodeficiency virus type I immobilized on a solid support for a time and under conditions sufficient for said antibody to form a complex with said immobilized human immunodeficiency virus antigen;

c) contacting said complex with an effective amount of a second antibody conjugated to an enzyme; and d) detecting binding of said second antibody to said complex.

14. The method of claim 13, wherein said enzyme is alkaline phosphatase.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 524 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met  Lys  Ile  Glu  Glu  Gly  Lys  Leu  Val  Ile  Trp  Ile  Asn  Gly  Asp  Lys
 1              5                        10                            15

Gly  Tyr  Asn  Gly  Leu  Ala  Glu  Val  Gly  Lys  Lys  Phe  Glu  Lys  Asp  Thr
               20                        25                  30

Gly  Ile  Lys  Val  Thr  Val  Glu  His  Pro  Asp  Lys  Leu  Glu  Glu  Lys  Phe
               35                        40                  45

Pro  Gln  Val  Ala  Ala  Thr  Gly  Asp  Gly  Pro  Asp  Ile  Ile  Phe  Trp  Ala
     50                       55                       60

His  Asp  Arg  Phe  Gly  Gly  Tyr  Ala  Gln  Ser  Gly  Leu  Leu  Ala  Glu  Ile
 65                      70                  75                            80

Thr  Pro  Asp  Lys  Ala  Phe  Gln  Asp  Lys  Leu  Tyr  Pro  Phe  Thr  Trp  Asp
                    85                  90                       95

Ala  Val  Arg  Tyr  Asn  Gly  Lys  Leu  Ile  Ala  Tyr  Pro  Ile  Ala  Val  Glu
              100                      105                     110

Ala  Leu  Ser  Leu  Ile  Tyr  Asn  Lys  Asp  Leu  Leu  Pro  Asn  Pro  Pro  Lys
              115                      120                     125

Thr  Trp  Glu  Glu  Ile  Pro  Ala  Leu  Asp  Lys  Glu  Leu  Lys  Ala  Lys  Gly
     130                      135                     140

Lys  Ser  Ala  Leu  Met  Phe  Asn  Leu  Gln  Glu  Pro  Tyr  Phe  Thr  Trp  Pro
145                           150                     155                 160
```

```
Leu  Ile  Ala  Ala  Asp  Gly  Gly  Tyr  Ala  Phe  Lys  Tyr  Glu  Asn  Gly  Lys
               165                     170                     175

Tyr  Asp  Ile  Lys  Asp  Val  Gly  Val  Asp  Asn  Ala  Gly  Ala  Lys  Ala  Gly
               180                     185                     190

Leu  Thr  Phe  Leu  Val  Asp  Leu  Ile  Lys  Asn  Lys  His  Met  Asn  Ala  Asp
               195                     200                     205

Thr  Asp  Tyr  Ser  Ile  Ala  Glu  Ala  Ala  Phe  Asn  Lys  Gly  Glu  Thr  Ala
          210                     215                     220

Met  Thr  Ile  Asn  Gly  Pro  Trp  Ala  Trp  Ser  Asn  Ile  Asp  Thr  Ser  Lys
225                     230                     235                          240

Val  Asn  Tyr  Gly  Val  Thr  Val  Leu  Pro  Thr  Phe  Lys  Gly  Gln  Pro  Ser
               245                     250                     255

Lys  Pro  Phe  Val  Gly  Val  Leu  Ser  Ala  Gly  Ile  Asn  Ala  Ala  Ser  Pro
               260                     265                     270

Asn  Lys  Glu  Leu  Ala  Lys  Glu  Phe  Leu  Glu  Asn  Tyr  Leu  Leu  Thr  Asp
               275                     280                     285

Glu  Gly  Leu  Glu  Ala  Val  Asn  Lys  Asp  Lys  Pro  Leu  Gly  Ala  Val  Ala
          290                     295                     300

Leu  Lys  Ser  Tyr  Glu  Glu  Glu  Leu  Ala  Lys  Asp  Pro  Arg  Ile  Ala  Ala
305                     310                     315                          320

Thr  Met  Glu  Asn  Ala  Gln  Lys  Gly  Glu  Ile  Met  Pro  Asn  Ile  Pro  Gln
                    325                     330                     335

Met  Ser  Ala  Phe  Trp  Tyr  Ala  Val  Arg  Thr  Ala  Val  Ile  Asn  Ala  Ala
               340                     345                     350

Ser  Gly  Arg  Gln  Thr  Val  Asp  Glu  Ala  Leu  Lys  Asp  Ala  Gln  Thr  Asn
               355                     360                     365

Ser  Ser  Ser  Gly  Ala  Arg  Ala  Ser  Val  Leu  Ser  Gly  Gly  Glu  Leu  Asp
          370                     375                     380

Arg  Trp  Glu  Lys  Ile  Arg  Leu  Arg  Pro  Gly  Gly  Lys  Lys  Lys  Tyr  Lys
385                     390                     395                          400

Leu  Lys  His  Ile  Val  Trp  Ala  Ser  Arg  Glu  Leu  Glu  Arg  Phe  Ala  Val
               405                     410                     415

Asn  Pro  Gly  Leu  Leu  Glu  Thr  Ser  Glu  Gly  Cys  Arg  Gln  Ile  Leu  Gly
               420                     425                     430

Gln  Leu  Gln  Pro  Ser  Leu  Gln  Thr  Gly  Ser  Glu  Glu  Leu  Arg  Ser  Leu
          435                     440                     445

Tyr  Asn  Thr  Val  Ala  Thr  Leu  Tyr  Cys  Val  His  Gln  Arg  Ile  Glu  Ile
          450                     455                     460

Lys  Asp  Thr  Lys  Glu  Ala  Leu  Asp  Lys  Ile  Glu  Glu  Glu  Gln  Asn  Lys
465                     470                     475                          480

Ser  Lys  Lys  Lys  Ala  Gln  Gln  Ala  Ala  Ala  Asp  Thr  Gly  His  Ser  Ser
               485                     490                     495

Gln  Val  Ser  Gln  Asn  Tyr  Pro  Ile  Val  Gln  Asn  Ile  Gln  Gly  Gln  Met
               500                     505                     510

Val  His  Gln  Ala  Ile  Ser  Pro  Arg  Thr  Leu  Asn  Gly
               515                     520
```

( 2 ) INFORMATION FOR SEQ ID NO:2:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Gly Ala Arg Ala Ser Val Leu Ser Gly Gly Glu Leu Asp Arg Trp Glu
 1               5                   10                  15

Lys Ile Arg Leu Arg Pro Gly Gly Lys Lys Lys Tyr Lys Leu Lys His
            20                  25                  30

Ile Val Trp Ala Ser Arg Glu Leu Glu Arg Phe Ala Val Asn Pro Gly
        35                  40                  45

Leu Leu Glu Thr Ser Glu Gly Cys Arg Gln Ile Leu Gly Gln Leu Gln
    50              55                      60

Pro Ser Leu Gln Thr Gly Ser Glu Glu Leu Arg Ser Leu Tyr Asn Thr
65              70                      75                  80

Val Ala Thr Leu Tyr Cys Val His Gln Arg Ile Glu Ile Lys Asp Thr
                85                  90                  95

Lys Glu Ala Leu Asp Lys Ile Glu Glu Glu Gln Asn Lys Ser Lys Lys
            100                 105             110

Lys Ala Gln Gln Ala Ala Ala
        115
```